United States Patent [19]
Mehra

[11] Patent Number: 5,265,601
[45] Date of Patent: Nov. 30, 1993

[54] DUAL CHAMBER CARDIAC PACING FROM A SINGLE ELECTRODE

[75] Inventor: Rahul Mehra, Stillwater, Minn.

[73] Assignee: Medtronic, Inc., Minneapolis, Minn.

[21] Appl. No.: 877,554

[22] Filed: May 1, 1992

[51] Int. Cl.⁵ .......................................... A61N 1/362
[52] U.S. Cl. ...................................................... 607/9
[58] Field of Search ................................ 128/419 PG

[56] References Cited

U.S. PATENT DOCUMENTS

| | | | |
|---|---|---|---|
| 3,557,796 | 5/1969 | Keller et al. | 128/419 PG |
| 3,595,242 | 5/1969 | Berkovits | 128/419 PG |
| 3,648,707 | 5/1972 | Greatbatch | 128/419 PG |
| 3,747,604 | 7/1973 | Berkovits | 128/419 PG |
| 4,312,355 | 1/1982 | Funke | 128/419 PG |
| 4,928,688 | 5/1990 | Mower | 128/419 PG |
| 5,129,394 | 7/1992 | Mehra | 128/419 PG |

OTHER PUBLICATIONS

"Atrial-Synchronized Demand Heart Pacing" by Fischler et al. in *IEEE Transactions on Bio-Medical Engineering*, vol. BME-16, No. 1, Jan. 1969.

Manual "Medtronic ® Coronary Sinus Pacing Leads--Models 6992 and 6992A", Sep., 1978.

*Primary Examiner*—William E. Kamm
*Assistant Examiner*—Scott M. Getzow
*Attorney, Agent, or Firm*—Reed A. Duthler; Harold R. Patton

[57] ABSTRACT

A method and apparatus for performing dual chamber cardiac pacing and sensing with a single pace/sense electrode situated in the coronary sinus or deep cardiac vein of a patient's heart. The pace/sense electrode is disposed at the end of a transvenous lead which extends from an implanted pacemaker, through the patient's right atrium, the patient's coronary sinus, and into the deep cardiac vein. Electrical cardiac signals received by the pace/sense electrode are applied to the inputs of two sense amplifiers, with one the sense amplifiers having a lower sensitivity threshold and the other having a higher sensitivity threshold. Electrical cardiac signals which exceed the lower sensitivity threshold but not the higher sensitivity threshold are interpreted as corresponding to atrial events, while electrical cardiac signals which exceed both the lower and higher sensitivity thresholds are interpreted as corresponding to ventricular events.

18 Claims, 3 Drawing Sheets

DUAL CHAMBER CARDIAC PACING FROM A SINGLE ELECTRODE

FIELD OF THE INVENTION

This invention relates generally to the field of cardiac pacemakers, and more particularly relates to dual chamber cardiac pacing.

BACKGROUND OF THE INVENTION

The activity of a normal, healthy heart consists of the synchronized contraction of the atria and ventricles of the heart. Blood is received into the atria, which contract, forcing the blood into the ventricles. Subsequent contraction of the ventricles then causes the blood to be pumped through the body and eventually returned to the atria. The contractions of the chambers of the heart are caused by coordinated electrical stimulation of portions of the cardiac muscle. The heartbeat cycle begins with the generation of an electrical impulse by a bundle of fibers located in the sinoatrial node of the heart, near the upper portion of the right atrium at the entrance to the superior vena cava. This impulse spreads across the atria, stimulating the atrial muscles and causing the atrial contraction which forces blood into the ventricles. An atrial contraction is manifested as the so-called "P-wave" in an electrocardiographic signal. The electrical impulse conducted through the atrial muscle is then received at the partition wall immediately beside the valve between the right atrium and right ventricle, at the atrio-ventricular or A-V node. The A-V node introduces a slight delay in the transmission of the electrical impulse to the ventricles. This A-V delay is typically on the order of 100-milliseconds or so. After the A-V delay, the electrical impulse is conducted to the ventricles, causing the ventricular contraction which is manifested as the "QRS complex" of an electrocardiographic signal. Subsequent repolarization and relaxation of the ventricular muscles occurs at the end of the cardiac cycle, which is manifested as the "T-wave" portion of an electrocardiographic signal.

For patients in which the above-described conduction of electrical impulses through the cardiac muscle is somehow impaired, a pacemaker can provide an artificial electrical stimulus where no natural electrical impulse is present. Thus, for example, a ventricular pacemaker can function to cause ventricular contractions in patients in which the natural electrical cardiac impulse is, for some reason, not transmitted across the A-V node. It is essential, however, that any artificial stimulating pulses be delivered at appropriated times, so that proper synchronization of atrial and ventricular action is maintained. In addition, it is known that electrical impulses being delivered to the cardiac muscle during the repolarization phase at the end of the cardiac cycle can cause the onset of tachyarrhythmias; it is therefore essential that the pacemaker be prevented from delivering stimulating pulses during the T-wave.

In order to maintain A-V synchrony, and to prevent delivery of pacing pulses at undesirable times, pacemakers are preferably capable of detecting either atrial activity, ventricular activity, or both, as manifested by the P-wave and QRS complex, respectively, of the electrocardiographic signal.

A wide variety of cardiac pacemakers are known and commercially available. Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events.

The North American Society of Pacing and Electrophysiology (NASPE) and the British Pacing and Electrophysiology Group (BPEG) have adopted a three-letter code which is used to describe the operative modalities of pacemakers. The first letter of the three letter code designates the chamber or chambers of the heart to which the pacemaker delivers pacing pulses; an "A" in the first position designates atrial pacing, a "V" designates ventricular pacing, and a "D" designates both atrial and ventricular pacing. Similarly, the second letter position designates the chambers of the heart from which the pacemaker senses electrical signals, and this second letter may be either an "A" (atrial sensing), a "V" (ventricular sensing), a "D" (atrial and ventricular sensing, or an "O" (no sensing). The third letter position designates the pacemaker's responses to sensed electrical signals; the pacemaker's response may either be to trigger the delivery of pacing pulses based upon sensed electrical cardiac signals (designated by a "T" in the third position), to inhibit the delivery of pacing pulses based upon sensed electrical cardiac signals (designated by an "I" in the third position), or both trigger and inhibit based upon sensed electrical cardiac signals (designated by a "D"). An "O" in the third position indicates that the pacemaker does not respond to sensed electrical signals.

Thus, for example, a "VVI" pacemaker delivers pacing stimuli to the ventricle of a patient's heart, senses electrical cardiac activity in the ventricle, and inhibits the delivery of pacing pulses when ventricular signals are sensed. A "DDD" pacemaker, on the other hand, delivers atrial pacing stimuli to both the atrium and ventricle of the patient's heart, senses electrical signals in both the atrium and ventricle, and both triggers and inhibits the delivery of pacing pulses based upon sensed electrical cardiac activity. The delivery of each pacing stimulus by a DDD pacemaker is synchronized with prior sensed or paced events. Other well-known types of pacemakers include AOO, VOO, AAI, VDD, and DVI.

Those types of pacemakers which are capable of delivering pacing pulses to both chambers of the heart (e.g., DDD and DVI pacemakers) are collectively referred to as "dual chamber" pacemakers. Presently, dual chamber pacing is most often accomplished with two electrodes, one being disposed in the patient's atrium and the other in the patient's ventricle. Two electrodes are also typically required if pacing is to be performed in one chamber and sensing in the other, as in the case of VAT pacing.

The two electrodes required for dual chamber or VAT pacing may either be disposed on two separate transvenous leads, or disposed at different points along the length of a unitary transvenous lead. Although in earlier dual chamber pacemakers, separate electrodes were required to perform pacing functions and sensing functions, thus requiring a total of four electrodes for a DDD pacemaker, it is commonly the case in more recent pacemakers that a single ventricular electrode is used for pacing, sensing, or both pacing and sensing in the ventricle, and a single atrial electrode is used for pacing, sensing, or both pacing and sensing in the atrium.

One reason that two electrodes have heretofore been deemed essential when sensing is to be performed in both chambers of the heart relates to the disparity of relative magnitudes of naturally occurring atrial electrical signals and ventricular electrical signals. As previously noted, the ventricular contraction constitutes the dominant portion of each cardiac cycle, and the electrical signals associated with ventricular contraction are accordingly of a greater magnitude than the electrical signals associated with atrial contraction. When sensing is performed from a ventricular electrode, a sensed ventricular signal will typically have a peak value on the order of 5 to 25-millivolts or so, whereas an atrial signal will typically be indiscernible or have a peak value of only 1 to 2-millivolts or so. Thus, atrial signals are typically not strong enough to be sensed by a single electrode situated in the ventricle. On the other hand, while the larger magnitude ventricular signals may be detectible by an electrode situated in the atrium, using a single electrode to receive both atrial and ventricular signals leads to difficulties in distinguishing between atrial and ventricular events, which is crucial to maintaining synchronous operation of a pacemaker. In practice, therefore, separate atrial and ventricular electrodes have been preferred.

Similarly, two electrodes have heretofore been deemed necessary when pacing is to be performed in both chambers of the heart, since from a ventricular electrode the pulse amplitude required to stimulate the atrium is unacceptably high.

Certain disadvantages to the use of two electrodes for pacing and/or sensing have been recognized. One disadvantage is that ensuring the correct placement of two leads can be difficult. Due to differences in the respective physical configurations of the right ventricle and right atrium, achieving a stable and effective placement of an electrode is more readily accomplished in the ventricle than in the atrium. A ventricular lead may be lodged near the apex of the right ventricle, and may even be attached to the ventricular wall by means of a tined or "screw-in" lead or the like. There is no corresponding physical structure in the atrium, however, which can provide similar support for an atrial electrode. Atrial lead stability is a problem, and even an atrial electrode, once properly placed, is susceptible to being moved or dislodged.

Another disadvantage of utilizing two electrodes for dual chamber or VAT pacing is the cost of two leads, or a two-electrode lead, as compared with a single, one-electrode lead. Moreover, two-lead pacing systems are relatively more complex than one-lead pacing systems, and are accordingly more prone to failure due to lead placement and mechanical failure.

In view of the foregoing, it is believed by the inventor that a method of accomplishing dual chamber sensing and pacing with a single electrode would be of great benefit to physicians and patients alike.

It is accordingly a feature of the present invention that a pacemaker is provided which utilizes a single electrode for sensing both atrial and ventricular electrical signals.

It is another feature of the present invention that a pacemaker is provided which utilizes a single electrode for delivering electrical pulses for stimulating the atrium of a patient's heart, and for stimulating the ventricle of a patient's heart.

It is a further feature of the present invention that means are provided in a pacemaker for reliably distinguishing between atrial electrical signals and ventricular electrical signals which are received on a single electrode.

SUMMARY OF THE INVENTION

The present invention relates to a novel system whereby a single transvenous electrode is utilized to perform atrial and ventricular sensing, as well as atrial and ventricular pacing.

A pacemaker in accordance with the present invention operates in conjunction with a single electrode which is disposed in the coronary sinus or deep cardiac vein, and is thus capable of detecting both atrial and ventricular electrical signals. Electrical cardiac signals received by this single electrode are first subjected to filtering and/or amplification, and then applied to the inputs of two sense amplifiers. The first sense amplifier is adjusted to have a lower threshold for sensing than the second, such that lower-magnitude atrial signals are sufficient only to exceed the threshold of the first sense amplifier, while higher-magnitude ventricular signals are sufficient to exceed the threshold of both amplifiers. Combinatorial logic receiving the output of the two sense amplifiers can thus generate separate digital signals for indicating the occurrence of ventricular and atrial events.

Further in accordance with the present invention, pacing stimulating pulses are delivered to the patient's heart via the same lead used for sensing, the electrode being disposed in the coronary sinus or deep cardiac vein. Atrial stimulating pulses are of relatively low magnitude, such that the ventricle is not stimulated. Ventricular stimulating pulses are of a relatively higher magnitude than the atrial stimulating pulses, but are delivered during the heart's natural atrial refractory period, such that only ventricular stimulation results.

BRIEF DESCRIPTION OF THE DRAWINGS

The foregoing and other features of the present invention will be best appreciated with reference to the detailed description of a specific embodiment of the invention, which follows, when read in conjunction with accompanying drawings, wherein.

DETAILED DESCRIPTION OF A SPECIFIC EMBODIMENT OF THE INVENTION

Figure 1:
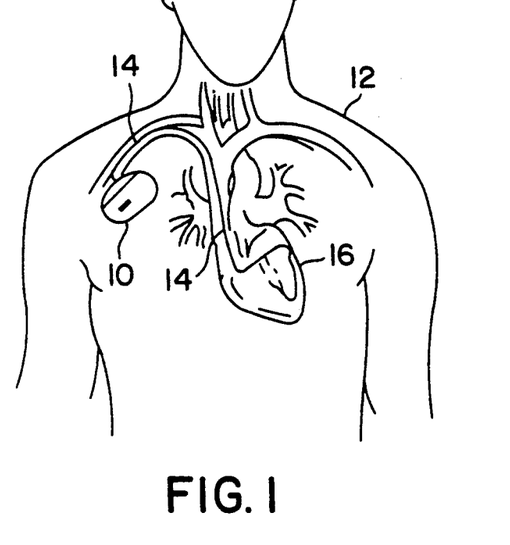
FIG. 1 is an illustration showing the placement of a pacemaker in accordance with the present invention within a patient's body.

FIG. 1 shows generally how a pacemaker 10 and transvenous lead 14 in accordance with one embodiment of the present invention may be implanted in the body of a patient 12. Pacemaker 10 is implanted in accordance with conventional practice in the area of the patient's collar-bone. Transvenous lead 14 is inserted into the patient, for example through a vein in the right arm or in the region of the collar-bone and passed by known techniques into the heart 16 by way of the superior vena cava.

Figure 2:
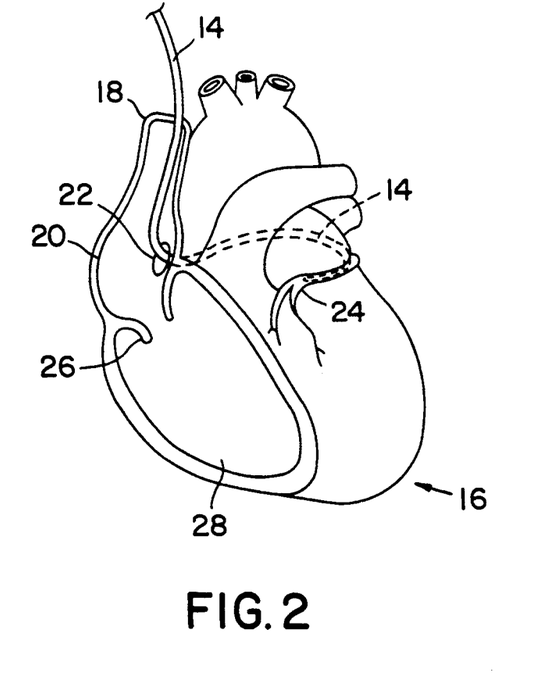
FIG. 2 is an illustration showing the distal end of the transvenous lead coupled to the pacemaker of FIG. 1.

Turning to FIG. 2, a more detailed illustration of heart 16 and the placement of lead 14 therein is shown. Lead 14 is introduced into heart 16 by way of the superior vena cava 18 and right atrium 20. It may be noted with reference to FIG. 2 that conventional ventricular pacing and sensing is accomplished with a lead which, unlike lead 14 of FIG. 2, extends through right atrium 20 and tricuspid valve 26, with its distal end disposed near the apex of right ventricle 28. In accordance with the present invention, on the other hand, lead 14 passes through the os 22 of the coronary sinus, such that the distal end of lead 14 is disposed within the deep cardiac vein 24. In FIG. 2, the portion of lead 14 passing through the coronary sinus is shown in phantom.

While the introduction of lead 14 into deep cardiac vein 24 is accomplished by known catheterization techniques, it is contemplated by the inventor that a slight bend on the end of the catheter may facilitate insertion into os 22 of the coronary sinus.

In accordance with the presently disclosed embodiment of the invention, the distal end of lead 14 is held in place within deep cardiac vein 24 by means of a stent or the like, which after introduction may be expanded by means of a catheter balloon such that the distal end of lead 14 is secured against the walls of deep cardiac vein 24 in electrical contact therewith. A stent suitable for the purposes of the presently disclosed embodiment of the invention is disclosed in co-pending U.S patent application Ser. No. 638,247, entitled "Implantable Electrode for Location Within a Blood Vessel", filed by the present inventor on Jan. 7, 1991 and held by the assignee of the present invention.

Figure 3:
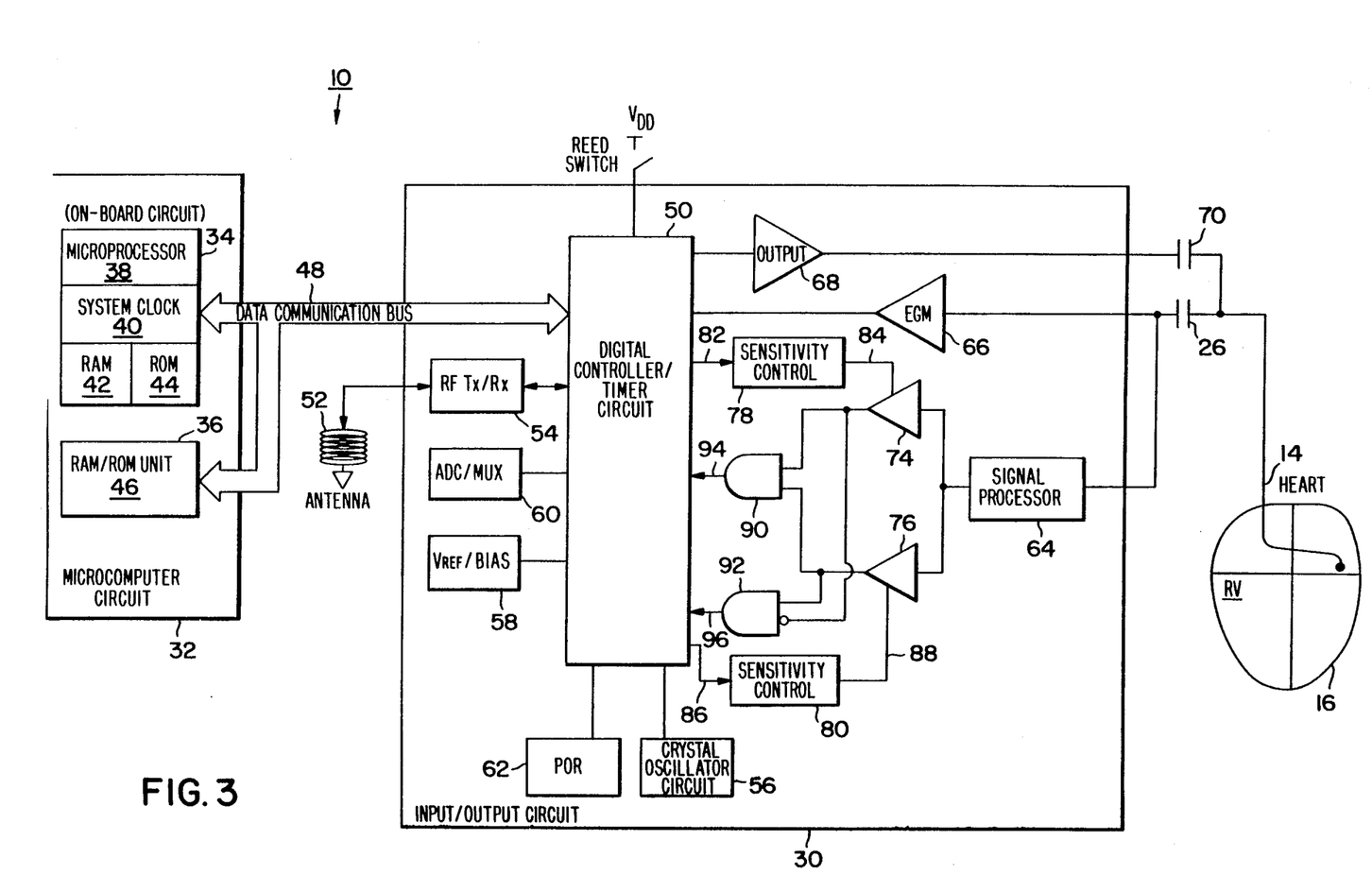
FIG. 3 is a diagram in block form of the pacemaker of FIG. 1.

In FIG. 3, a block diagram of pacemaker 10 from FIG. 1 is shown. Although the present invention is described in conjunction with a pacemaker 10 having a microprocessor-based architecture, it will be understood that it could be implemented in any logic based, custom integrated circuit architecture, if desired. It will also be understood that the present invention may be utilized in conjunction with other implantable medical devices, such as cardioverters, defibrillators and the like.

Input/output circuit 30 in FIG. 3 contains the operating input and output analog circuits for digital controlling and timing circuits necessary for the detection of electrical signals derived from heart 16, such as the cardiac electrogram (EGM), as well as for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. Off-board circuit 36 includes an off-board RAM/ROM unit 46. Microcomputer circuit 32 is coupled by data communication bus 48 to a digital controller/timer circuit 50. Microcomputer circuit 32 may be fabricated of custom integrated circuit devices augmented by standard RAM/ROM components.

It will be understood that the electrical components represented in FIG. 3 are powered by an appropriate implantable battery power source, not shown, in accordance with common practice in the art.

An antenna 52 is connected to input/output circuit 30 for purposes of uplink/downlink telemetry through RF transmitter/receiver (RF TX/RX) unit 54. Telemetering both analog and digital data between antenna 52 and an external device, such as an external programmer (not shown), is accomplished in the presently disclosed embodiment by means of all data first being digitally encoded and then pulse-position modulated on a damped RF carrier, as substantially described in co-pending U.S. patent application Ser. No. 468,407, filed on Jan. 22, 1990, entitled "Improved Telemetry Format", which is assigned to the assignee of the present invention and which is incorporated herein by reference.

A crystal oscillator circuit 56, typically a 32,768-Hz crystal-controlled oscillator, provides main timing clock signals to digital controller/timer circuit 50. A Vref/Bias circuit 58 generates stable voltage reference and bias currents for the analog circuits of input/output circuit 30. An analog-to-digital converter/multiplexor (ADC/MUX) unit 60 digitizes analog signals and voltages to provide telemetry and battery end-of-life (EOL) replacement function. A power-on-reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input/output circuit 30.

In the embodiment of FIG. 3, electrical cardiac signals are conducted along lead 14 and applied, via coupling capacitor 26 to signal processor circuit 64, which performs basic filtering and/or amplification on the received cardiac signal. Electrical cardiac signals from lead 14 are also applied, via coupling capacitor 26 to and electrogram (EGM) amplifier 66. The electrogram signal developed by EGM amplifier 66 is used in those occasions when the implanted device is being interrogated by an external programmer, not shown, in order to transmit by uplink telemetry a representation of the analog electrogram of the patient's electrical heart activity as described in U.S. Pat. No. 4,556,063, issued to Thompson et al., assigned to the assignee of the present invention and incorporated herein by reference. An output pulse generator 68 provides pacing stimuli to the patient's heart 16 via coupling capacitor 70 and lead 14 in response to a pacing trigger signal developed by digital controller/timer circuit 50 each time the escape interval times out, or an externally transmitted pacing command has been received, or in response to other stored commands as is well known in the pacing art.

It is to be understood, of course, that pacemaker 10 may include additional components, such as activity sensors, pressure sensors, and the like, not shown in FIG. 3 for further enabling pacemaker 10 to respond to the physiological requirements of the patient.

The processed electrical cardiac signal produced by signal processor circuit 64 is applied to the inputs of two sense amplifiers 74 and 76. Sensitivity control circuits 78 and 80 function to control the sensitivity threshold of sense amplifiers 74 and 76, respectively, as directed by digital controller/timer circuit 50. In particular, digital controller/timer circuit 50 issues control signals on control line 82 (which may comprise multiple conductors) to sensitivity control circuit 78, which signals instruct sensitivity control circuit to increase or decrease the sensitivity threshold of sense amplifier 74. Sensitivity control circuit 78 causes the sensitivity threshold of sense amplifier 74 by means of control signals issued on line 84 (which may similarly comprise multiple conductors). In a similar fashion, control signals on control line 86 instruction sensitivity control circuit 80 to increase or decrease the sensitivity threshold of sense amplifier 76, which is accomplished by means of control signals issued by control circuit 80 on line 88. In this way, the sensitivity thresholds of respective sense amplifiers 74 and 76 may be independently selected by digital controller/timer circuit 50.

The outputs of sense amplifiers 74 and 76 are applied to a simple digital logic circuit comprising logical AND gates 90 and 92, as shown in FIG. 3. The arrangement of sense amplifiers with separately controllable sensitivity thresholds and AND gates 90 and 92 allows for the differentiation between atrial and ventricular signals conducted on lead 14. This differentiation is possible due to the relative magnitudes of atrial and ventricular signals, and in particular, due to the fact that ventricular signals detected in the coronary sinus or deep cardiac vein have a significantly greater magnitude than atrial signals at that location. In accordance with the presently disclosed embodiment of the invention, the sensitivity threshold of sense amplifier 74 is set at a higher level than the sensitivity threshold of sense amplifier 76; that is, sense amplifier 74 is less sensitive to received electrical signals than sense amplifier 76. If an incoming filtered signal from signal processor 64 is detected by both sense amplifiers 74 and 76, then this is assumed to be a ventricular signal. If, on the other hand, an incoming filtered signal is detected by sense amplifier 76 only (sense amplifier 76 being more sensitive than sense amplifier 74), then this is assumed to be an atrial signal which is of insufficient magnitude to be sensed by sense amplifier 74. It should be noted that there is no situation in which only sense amplifier 74, and not sense amplifier 76, will detect an incoming signal, since any signal which is sufficient to exceed the sensitivity threshold of sense amplifier 74 will also exceed the lower sensitivity threshold of sense amplifier 76.

As shown in FIG. 3, the outputs of both amplifiers 74 and 76 are applied to non-inverted inputs to AND gate 90. The output of sense amplifier 76 is also applied to a non-inverted input to AND gate 92. The output of sense amplifier 74, however, is applied to an inverted input of to AND gate 92. As would be apparent to one of ordinary skill in the design of digital logic circuits, this configuration of AND gates 90 and 92, results in the output of AND gate 90 being at a logical high level and the output of AND gate 92 being at a logical low level whenever both sense amplifiers detect an incoming filtered signal; however, the output of AND gate 90 goes to a logical low level and the output of AND gate 92 goes to a logical high level whenever sense amplifier 76, but not sense amplifier 78, detects an incoming filtered signal.

Thus, the output of AND gate 90, which is conducted via line 94 to digital controller/timer circuit 50, is asserted in response to a sensed ventricular signal, whereas the output of AND gate 92, which is conducted to digital controller/timer circuit 50 on line 96, is asserted in response to a sensed atrial signal.

With the signals on lines 94 and 96 thus providing an indication of the occurrence of each sensed atrial and ventricular event, digital controller/timer circuit can carry out dual chamber (e.g., DDD, DVI) and single chamber (e.g., VDD) pacing algorithms, as are commonly known in the art. In accordance with the presently disclosed embodiment of the invention, pacing stimuli are delivered to the patient's heart 16 by means of the same lead 14 used for sensing, the distal end of lead 14 being disposed in the deep cardiac vein, as previously described with reference to FIG. 2. The inventor has observed that with a lead disposed in this manner, dual chamber pacing can be carried out by delivering two stimuli of different magnitudes and separated by an appropriate A-V delay. During each cardiac cycle, the first (i.e., atrial) stimulus would be of a lower magnitude and would therefore be sufficient to stimulate the atrium only. A second (i.e., ventricular) stimulus, being of a higher magnitude, would be sufficient to stimulate the ventricle. This second stimulus will not stimulate the atrium if it is delivered soon enough after a sensed or paced atrial contraction such that the second stimulus occurs during the atrium's natural refractory period, during which time the atrial muscles are rendered insensitive to electrical stimuli.

Figure 4:
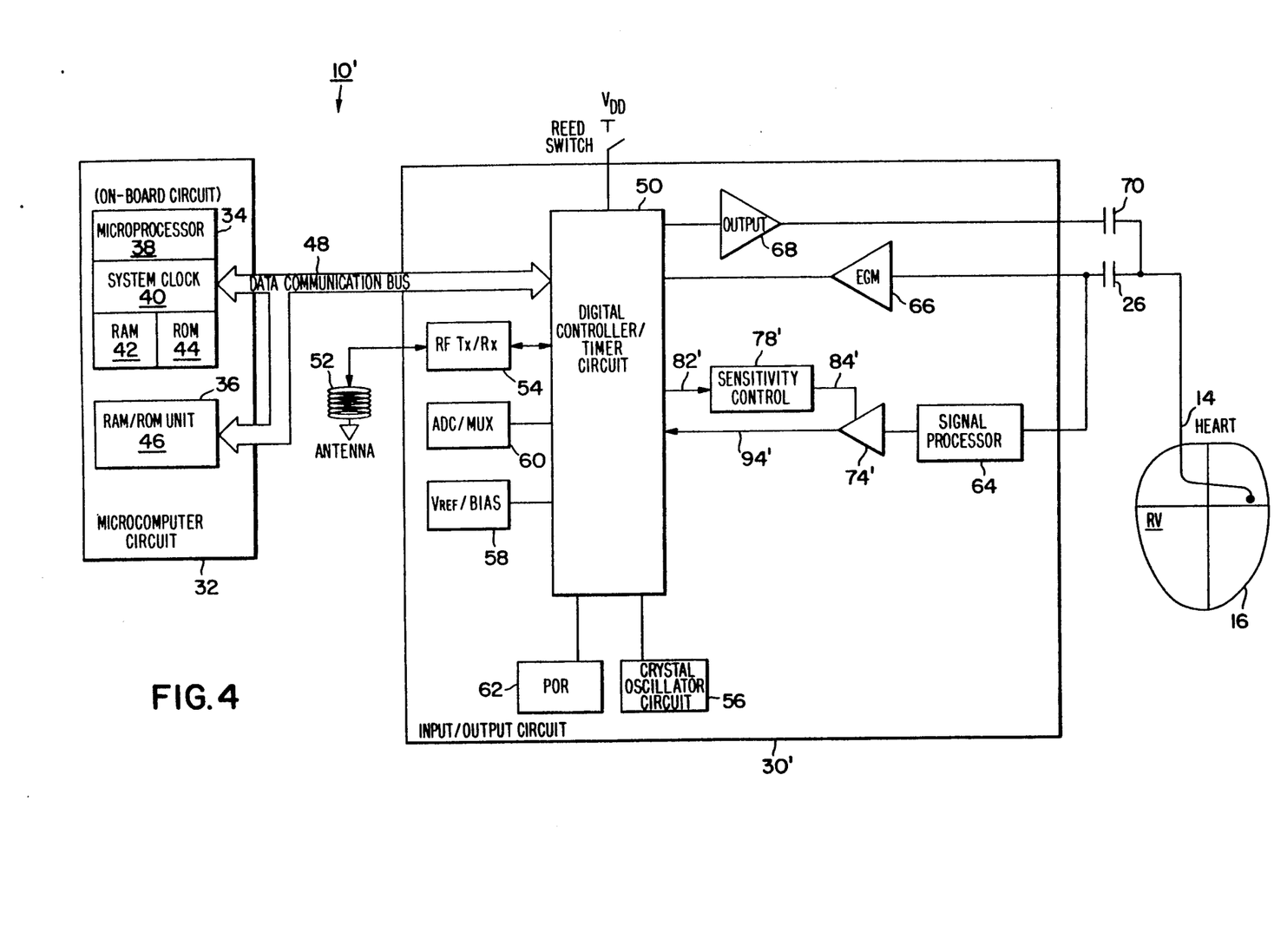
FIG. 4 is a diagram in block form of an alternative embodiment of a pacemaker in accordance with the present invention.

An alternative embodiment of the present invention contemplated by the inventor is shown in FIG. 4, wherein components which are identical to those of FIG. 3 have retained identical reference numerals. In the pacemaker 10' of FIG. 4, input/output circuit 30' includes only a single sense amplifier 74' which receives the output of signal processing circuitry 64. The sensitivity threshold of sense amplifier 74' is controlled by sensitivity control circuitry 78', which receives instructions on line 82' (which may comprise multiple conductors) from digital controller/timer circuit 50. The output of sense amplifier 74' is conducted on line 94' to digital controller/timer circuit 50.

Operation of pacemaker 10' of FIG. 4 proceeds as follows: initially, digital controller/timer circuit 50 instructs sensitivity control circuit 78 to set the sensitivity threshold at a first, low level, appropriate for the purposes of detecting atrial events (i.e., the same threshold setting as for sense amplifier 76 in the embodiment of FIG. 3). When an atrial event occurs, a pulse will be produced by sense amplifier 74' and will be received by digital controller/timer circuit 50. Upon receipt of this pulse, digital controller/timer circuit 50 will immediately instruct sensitivity control circuit 78' to increase the sensitivity threshold of sense amplifier 74' to a second, higher threshold voltage, appropriate for detecting ventricular events but not atrial events (i.e., the same threshold setting as for sense amplifier 74 in the embodiment of FIG. 3). Thereafter, any pulse received by digital controller/timer circuit 50 will correspond to a ventricular event. As would be apparent to one of ordinary skill in the pacing art, if a ventricular event is not sensed within an appropriate A-V time interval following detection of an atrial event, a ventricular pacing pulse may be delivered by output pulse generator 68.

After either a sensed ventricular event or the delivery of a ventricular pacing pulse, digital controller/timer circuit 50 will instruct sensitivity control circuit 78' to reduce the sensitivity threshold of sense amplifier 74' to the first, atrial, level. If no atrial event is sensed within an appropriate V-A time interval, an atrial pacing pulse may be delivered, and the entire process repeated.

From the foregoing detailed description of particular embodiments of the invention, it should be apparent that a pacemaker capable of dual chamber pacing and sensing using a single transvenous lead has been disclosed. While a particular embodiment of the invention has been disclosed in detail, it is to be understood that various alterations, modifications, or substitutions may be made therein without departing from the spirit and scope of the present invention, as defined in the appended claims.

In particular, it is contemplated by the inventor that the desired chamber of the heart (i.e., atrium or ventricle) can be selectively recruited or captured by the pacemaker, by adjustably varying the respective atrial and/or ventricular stimuli to deliver a stimulus which attains the desired chamber's pacing threshold (whether measured as a voltage, current or energy threshold). For example, the output parameters of a stimulus pulse may be varied by adjusting its pulse width, or amplitude (i.e., current or voltage).

It is well known, for example, that cardiac pacing threshold is the minimal electrical stimulation required to cause cardiac muscle contraction, and that voltage threshold is the most commonly used measurement of pacing threshold. However, other less frequently used pacing thresholds include current threshold and energy threshold. Energy threshold is the product of voltage, current and pulse duration at threshold. It gives the total picture of energy required for depolarization and is usually expressed in micro-joules.

Strength duration curves, such as those disclosed in Moses et al., *A Practical Guide to Cardiac Pacing*, Ed. 3, Boston, 1991, Little Brown and Co., illustrate the relationship between pulse width or pulse duration and voltage threshold. The relationship between pulse width and voltage threshold demonstrates that greater voltage is required to stimulate the heart as the pulse width becomes more narrow. It is thus evident from the relationship, and also well known in the art that pacing threshold may be measured in terms of energy threshold.

What is claimed is:

1. A pacemaker, comprising:
   a pulse generator, for producing cardiac stimulating pulses;
   a lead, coupled to said pulse generator via a first coupling capacitor, having an electrode on its distal end, said electrode being disposed in a venous channel of a patient's heart;
   signal processing circuitry means, coupled to said lead via a second coupling capacitor, for receiving from said lead electrical cardiac signals received by said electrode in said venous channel and said signal processing circuitry filtering and amplifying said cardiac signals to produce a processed cardiac output signal;
   a first sense amplifier, coupled to said signal processing circuitry and receiving said processed cardiac output signal, said first sense amplifier having a first sensitivity threshold voltage such that electrical signals having a voltage level below said first sensitivity threshold are not amplified by said first sense amplifier;
   a second sense amplifier, coupled to said signal processing circuitry and receiving said processed cardiac output signal, said second sense amplifier having a second sensitivity threshold voltage, higher than said first sensitivity threshold voltage, such that electrical signals having a voltage level below said second sensitivity threshold are not amplified by said second sense amplifier;
   logic circuitry, having first and second inputs for receiving first and second input signals, and having first and second outputs for producing first and second output signals, said first and second inputs coupled to said first and second sense amplifiers, respectively;
   such that a processed cardiac output signal which has a voltage which exceeds said first sensitivity threshold voltage but does not exceed said second sensitivity threshold voltage causes said first output signal, and not said second output signal, to be asserted, and such that a processed electrical cardiac signal which has a voltage which exceeds both said first and second sensitivity threshold voltages causes said second output signal and not said first output signal to be asserted;
   said pacemaker further comprising controlling circuitry means, receiving said first and second output signal, for controlling delivery of cardiac pacing pulses, and for causing a cardiac pacing pulse to be delivered from said electrode at a first stimulating energy level if said first output signal is not asserted within a first predetermined time interval following assertion of said second output signal;
   said controlling circuitry means further causing a cardiac pacing pulse to be delivered at a second stimulating energy level, higher than said first stimulating energy level, if said second output signal is not asserted within a second predetermined time interval following assertion of said first output signal.

2. A pacemaker in accordance with claim 1, wherein said venous channel comprises the coronary sinus of said heart.

3. A pacemaker in accordance with claim 2, wherein said venous channel comprises the deep cardiac vein of said heart.

4. A method of pacing a patient's heart via a single pacing/sensing electrode comprising the steps of:
   (a) disposing said electrode in a venous channel of said heart;
   (b) applying cardiac signals received by said electrode to inputs of first and second sense amplifiers having first and second sensing thresholds voltages, respectively, said first sensing threshold voltage being lower than said second sensing threshold voltage;
   (c) asserting an atrial event indicating signal when said cardiac signals exceed the sensing threshold of said first sense amplifier and do not exceed the sensing threshold of said second sense amplifier;
   (d) asserting a ventricular event indicating signal when said cardiac signals exceed the sensing thresholds of both said first and second sense amplifier;
   (e) delivering a pacing pulse from said electrode at a first, lower stimulating energy level if said atrial event indicating signal is not asserted within a first predetermined time interval following assertion of said ventricular event indicating signal; and
   (f) delivering a pacing pulse from said electrode at a second, higher stimulating energy level if said ventricular event indicating signal is not asserted within a second predetermined time interval following assertion of said atrial event indicating signal.

5. A method in accordance with claim 4, wherein said step of disposing said electrode in a venous channel of said heart comprises disposing said electrode in the coronary sinus of said heart.

6. A method in accordance with claim 4, wherein said step of disposing said electrode in a venous channel of said heart comprises disposing said electrode in the deep cardiac vein of said heart.

7. A method in accordance with claim 4, further comprising the steps of:
   (g) inhibiting delivery of a pacing pulse from said electrode at said first, lower stimulating energy level if said atrial event indicating signal is asserted within said first predetermined time interval following assertion of said ventricular event indicating signal; and
   (h) inhibiting delivery of a pacing pulse from said electrode at said second, higher stimulating energy level if said ventricular event indicating signal is asserted within said second predetermined time interval following assertion of said atrial event indicating signal.

8. A method in accordance with claim 7, wherein said step of disposing said electrode in a venous channel of said heart comprises disposing said electrode in the coronary sinus of said heart.

9. A method in accordance with claim 7, wherein said step of disposing said electrode in a venous channel of said heart comprises disposing said electrode in the deep cardiac vein of said heart.

10. A method of pacing a patients heart via a single pacing/sensing electrode comprising the steps of:
    (a) disposing said electrode in a venous channel of said heart;
    (b) applying electrical cardiac signals received by said electrode to the input of a sense amplifier having a selectable sensing threshold voltage;
    (c) initially setting the sensing threshold voltage of said sense amplifier to a first level;
    (d) asserting a ventricular event indicating signal if said electrical cardiac signals exceed said first sensing threshold voltage level within a first predetermined time period following assertion of an atrial event indicating signal;
    (e) delivering a cardiac stimulating pulse from said electrode at a first stimulating energy level if said electrical cardiac signals do not exceed said first sensing threshold voltage level within said first predetermined time interval following assertion of said atrial event indicating signal;
    (f) re-setting the sensing threshold voltage of said sense amplifier to a second threshold voltage level, lower than said first sensing threshold voltage level, if said ventricular event indicating signal is asserted and if a cardiac stimulating pulse is delivered at said first stimulating voltage level;
    (g) asserting an atrial event indicating signal if said electrical cardiac signals exceed said second sensing threshold voltage level within a second predetermined time interval;
    (h) delivering a cardiac stimulating pulse from said electrode at a second stimulating energy level, lower than said first stimulating voltage level, if said electrical cardiac signals do not exceed said second sensing threshold voltage level within said second predetermined time interval;
    (i) re-setting the sensing threshold voltage of said sense amplifier to said first sensing threshold level if said atrial event indicating signal is asserted and if a cardiac stimulating pulse is delivered at said second, lower stimulating voltage level;
    (j) continuously repeating steps (d) through (i) above.

11. A method in accordance with claim 10, wherein said step of disposing said electrode in a venous channel of said heart comprises disposing said electrode in the cardiac sinus of said heart.

12. A method in accordance with claim 10, wherein said step of disposing said electrode in a venous channel of said heart comprises disposing said electrode in the deep cardiac vein of said heart.

13. A method of pacing the atrium and ventricle of a human heart, comprising:
    locating an electrode with respect to said human heart in a position such that the pacing threshold of said atrium of said human heart, at said position, is lower than the pacing threshold of said ventricle of said human heart, at said position; and
    sequentially delivering pacing pulses to said electrode to stimulate said atrium and said ventricle, said pacing pulses comprising a first pulse delivered at a level in excess of said pacing threshold of said atrium but less than said pacing threshold of said ventricle, followed by a second pulse delivered at a level in excess of said pacing threshold of said ventricle.

14. A method according to claim 13 wherein said step of locating said electrode comprises locating said electrode in the coronary sinus or great vein of said human heart.

15. A method according to claim 13 or claim 14 further comprising the step of sensing electrical activity of said human heart, using said electrode, and the step of controlling the timing of delivery of said pacing pulses as a function of said sensed electrical activity.

16. A method of pacing the ventricle of a human heart in synchrony with the atrium of a human heart, comprising:
    locating an electrode in a position adjacent the atrium and ventricle of said human heart, at which electrical signals from said atrium of said human heart may be sensed and at which stimulation of said ventricle of said human heart may be accomplished;
    sensing electrical activity of the atrium of said human heart; and
    following sensing of electrical activity in the atrium of said human heart, using said electrode, delivering a pacing pulse to said electrode to stimulate the ventricle of said human heart.

17. A method according to claim 16 wherein said step of locating said electrode comprises locating said electrode in a coronary sinus or great vein of said human heart.

18. A method according to claim 16 or claim 17 wherein said method further comprises the step of delivering a reduced amplitude pacing pulse to said electrode to stimulate said atrium of said patient's heart in the absence of sensed electrical activity in the atrium of said patient's heart.

* * * * *

UNITED STATES PATENT AND TRADEMARK OFFICE
CERTIFICATE OF CORRECTION

PATENT NO. : 5,265,601
DATED : November 30, 1993
INVENTOR(S) : Rahul Mehra

It is certified that error appears in the above-indentified patent and that said Letters Patent is hereby corrected as shown below:

Column 9, Lines 53-54, delete "said signal processing circuitry", and insert in its place --for--.

Column 10, Line 22, delete "signal,", and insert in its place --signals,--.

Signed and Sealed this

Twentieth Day of September, 1994

Attest:

BRUCE LEHMAN

Attesting Officer

Commissioner of Patents and Trademarks